(12) United States Patent
Goldenshtein et al.

(10) Patent No.: US 7,400,390 B2
(45) Date of Patent: Jul. 15, 2008

(54) INSPECTION SYSTEM AND A METHOD FOR AERIAL RETICLE INSPECTION

(75) Inventors: Alex Goldenshtein, Ness-Ziona (IL); Emanuel Elyasaf, Rehovot (IL)

(73) Assignee: Applied Materials, Israel, Ltd., Rehovot (IL)

( * ) Notice: Subject to any disclaimer, the term of this patent is extended or adjusted under 35 U.S.C. 154(b) by 74 days.

(21) Appl. No.: 10/999,227

(22) Filed: Nov. 29, 2004

(65) Prior Publication Data

US 2006/0114453 A1 Jun. 1, 2006

(51) Int. Cl.
*G01N 21/00* (2006.01)

(52) U.S. Cl. .................................. 356/237.2
(58) Field of Classification Search ............. 356/237.1, 356/237.2

See application file for complete search history.

(56) References Cited

U.S. PATENT DOCUMENTS

| | | | |
|---|---|---|---|
| 3,614,232 A | 10/1971 | Mathisen | |
| 4,844,617 A | 7/1989 | Kelderman et al. | |
| 5,602,619 A | 2/1997 | Sogard | |
| 5,659,168 A | 8/1997 | Dey et al. | |
| 5,768,017 A | 6/1998 | King et al. | |
| 5,859,424 A | 1/1999 | Norton et al. | |
| 6,064,477 A * | 5/2000 | Matsumoto et al. | 356/237.2 |
| 6,081,325 A | 6/2000 | Leslie et al. | |
| 6,133,986 A | 10/2000 | Johnson | |
| 6,177,980 B1 | 1/2001 | Johnson | |
| 6,248,988 B1 | 6/2001 | Krantz | |
| 6,268,093 B1 * | 7/2001 | Kenan et al. | 430/30 |
| 6,459,484 B1 | 10/2002 | Yokoi | |
| 6,466,315 B1 * | 10/2002 | Karpol et al. | 356/237.4 |
| 6,540,145 B2 | 4/2003 | Gurevich et al. | |
| 6,757,645 B2 * | 6/2004 | Chang et al. | 703/13 |
| 6,803,554 B2 * | 10/2004 | Ye et al. | 250/208.1 |
| 6,911,347 B2 | 6/2005 | Higgs | |
| 7,027,143 B1 * | 4/2006 | Stokowski et al. | 356/237.2 |
| 7,072,502 B2 * | 7/2006 | Hemar et al. | 382/144 |
| 7,123,356 B1 * | 10/2006 | Stokowski et al. | 356/237.2 |
| 7,133,119 B1 * | 11/2006 | Pettibone et al. | 355/71 |
| 7,271,891 B1 * | 9/2007 | Xiong et al. | 356/237.4 |
| 2003/0132405 A1 | 7/2003 | Some | |

* cited by examiner

*Primary Examiner*—Patrick Connolly
*Assistant Examiner*—Jonathan Skovholt
(74) *Attorney, Agent, or Firm*—Tarek N. Fahmi

(57) ABSTRACT

A method for inspecting a reticle, that includes the following stages: providing a reticle designed to be exposed by light of a first wavelength during a photolithography process; defining optical characteristics of an inspection system, whereas the optical characteristics include a second wavelength that differs from the first wavelength; and configuring an inspection system in response to the defined optical characteristics. An inspection system that includes: an illumination path adapted to direct light of a second wavelength towards a reticle designed to be exposed by light of a first wavelength during a photolithography process; a collection path adapted to collect light transmitted through the reticle; whereas at least one of the illumination path and collection path is configurable such that the inspection system emulates the photolithographic process while utilizing light of the second wavelength.

10 Claims, 3 Drawing Sheets providing a reticle designed to be exposed by light of a first wavelength during a photolithography process
310 defining optical characteristics of an inspection system, wherein the optical characteristics include a second wavelength that differs from the first wavelength
320 configuring an inspection system in response to the defined optical characteristics
330 illuminating at least a portion of the reticle with light of the second wavelength to provide at least one image
340

INSPECTION SYSTEM AND A METHOD FOR AERIAL RETICLE INSPECTION

FIELD OF THE INVENTION

This invention relates to systems and methods for aerial imaging, and especially for method and systems that are able to inspect different reticles designed to be exposed to light of different wavelengths.

BACKGROUND OF THE INVENTION

Modern microelectronic devices are commonly produced using a photolithographic process. In this process, a semiconductor wafer is first coated with a layer of photoresist. This photoresist layer is then exposed to illuminating light using a photomask (for simplicity, the terms photomask, mask, and reticle will be used here interchangeably) and subsequently developed. After the development, non-exposed photoresist is removed, and the exposed photoresist produces the image of the mask on the wafer. Thereafter, the uppermost layer of the wafer is etched. Thereafter, the remaining photoresist is stripped. For multilayer wafers, the above procedure is then repeated to produce subsequent patterned layers. Reticles are designed such as to produce a certain pattern once they are illuminated by light of a certain wavelength.

Modern reticle inspection systems include an illumination path for illumination an inspected reticle as well as a collection path that directs light towards sensors. An inspection system is characterized by its resolution, its illumination numerical aperture $NA_i$ and its collection numerical aperture $NA_c$. As a rule of thumb, the resolution R of the inspection system is responsive to the ratio between the wavelength $\lambda$ of the illuminating light and the collection numerical aperture $NA_c$. The ratio between $NA_i$ and $NA_c$ is also known as sigma ($\sigma$). Sigma also provides an indication about the coherence of the light generated by the inspection system.

U.S. Pat. No. 6,268,093 of Kenan et al., titled "Method for reticle inspection using aerial imaging", which is incorporated herein by reference describes a prior art aerial reticle inspection system.

The resolution of an inspection system has to be responsive to the size of integrated circuit structures and to the size of possible defects. As these structures get smaller the resolution of the reticle inspection system has to improve. The resolution is usually improved by using ultraviolet and even deep ultra violet light. In the future, inspection systems will be capable of using extreme ultra violet light.

During a photolithography process the reticle is illuminated with light of a certain wavelength. Reticle inspection systems and especially aerial reticle inspection systems use light that has a wavelength that is the same of the light used during the photolithography process. For example, if reticles are illuminated with a 248 nm light then the inspection system will illuminate a reticle by a use 248 nm light. An aerial inspection system will emulate the photolithography process that uses light of that certain wavelength.

Typically, a single integrated circuit manufacturer produces integrated circuits in various manufacturing process that may differ by their illuminating light wavelength. Thus, a single FAB can apply both new manufacturing processes as well as legacy manufacturing processes.

Thus, there is a need to provide systems and methods for aerial inspection of reticles, whereas the systems and methods can be applied to inspect reticles that are exposed under different wavelengths during a photolithography process.

SUMMARY OF THE INVENTION

A method for inspecting a reticle, that includes the following stages: (i) providing a reticle designed to be exposed by light of a first wavelength during a photolithography process; (ii) defining optical characteristics of an inspection system, whereas the optical characteristics include a second wavelength that differs from the first wavelength; and (iii) configuring an inspection system in response to the defined optical characteristics.

An inspection system that includes: (i) an illumination path adapted to direct light of a second wavelength towards a reticle designed to be exposed by light of a first wavelength during a photolithography process; and (ii) a collection path adapted to collect light transmitted through the reticle. Whereas the illumination path and/or the collection path are configurable such that the inspection system emulates the photolithographic process while utilizing light of the second wavelength.

BRIEF DESCRIPTION OF THE DRAWINGS

FIG. 3 is a flow chart illustrating a method for reticle inspection.

DETAILED DESCRIPTION OF THE DRAWINGS

Figure 1:
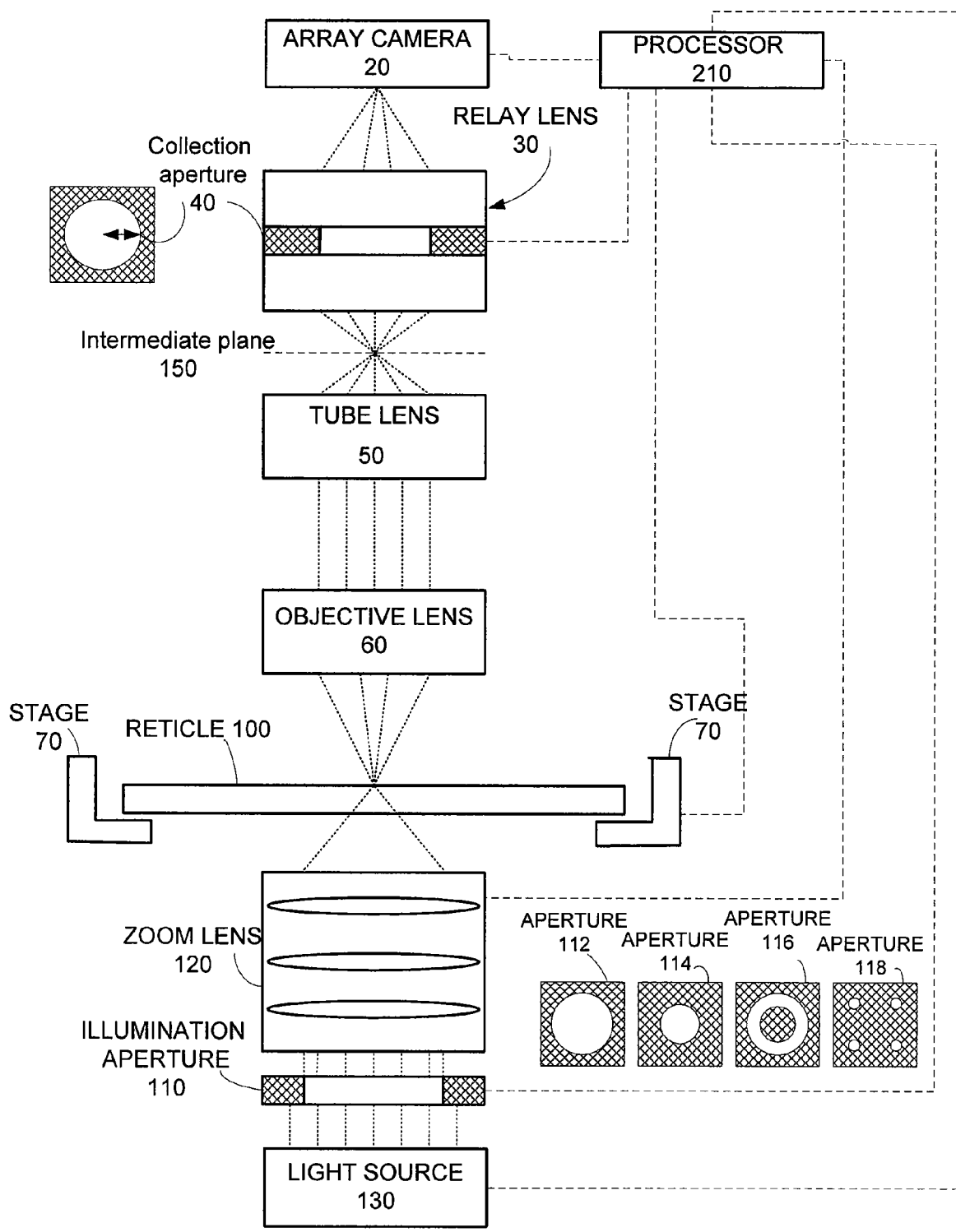
FIG. 1 is a schematic diagram of an inspection system according to an embodiment of the present invention.

FIG. 1 illustrates an inspection system 10 as well as an exemplary inspected reticle 100, according to an embodiment of the invention. System 10 includes various optical components that form an illumination path as well as a collection path.

Inspection system 10 may include various components and modules such as auto-focus module, human machine interface unit, vacuum chamber, storage unit, interferometer and the like, that are not illustrated for simplicity of explanation.

The illumination path includes a light source 130, illumination aperture 110 and zoom lens 120. The light source 130 can be a continuous or a pulsating light source such as an ultraviolet, deep ultraviolet or an extreme ultra violet laser. The light source 130 conveniently includes speckle reduction optics. Light source 130 conveniently includes collimating optics. Collimating optics and speckle reduction optics are known in the art and require no further explanation.

Collimated light passes through an illumination aperture 110. The size and shape of the illumination aperture 110 can be altered in various manners. For example, a cassette of apertures may be used such as to position a selected aperture (for example round shaped aperture 110) within the path of the illuminating light. FIG. 1 illustrates various possible apertures such as round shaped apertures 112 and 114 that differ by size, annular aperture 116 and multiple apertures 118. It is noted that the illumination aperture can be defined by an adjustable component such as a liquid crystal array, an array of mirrors and the like.

The zoom lens 120 includes multiple lenses that can be moved from location to another, such as to alter the magnification of the zoom lens 120 and to provide a magnified image of the illumination aperture.

The numerical aperture of the illumination path $NA_i$ is defined by controlling the illumination aperture 110 and/or by controlling the lenses that form zoom lens 120.

The light that passes through the zoom lens 120 is directed towards the reticle 100 such as to illuminate it in a transmissive mode. Reticle 100, and especially the upper surface of reticle 100 define a starting plane of the collection path. The collection optics relays a portion of the image formed in this starting plane, as defined by the collection aperture 40, to one or more two-dimensional sensor arrays such as CCD cameras, TDI cameras and the like. FIG. 1 illustrates a single camera but splitting optics can split collected light towards more than a single camera. A multiple CCD camera configuration is illustrated, for example, in U.S. Pat. No. 6,268,093, which is incorporated herein by reference.

The collection path includes an objective lens 60 that is followed by tube lens 50 and relay lens 30 (that includes a collection aperture 40). The objective lens 60 and the tube lens 50 relay the image formed at the starting plane to an intermediate plane 150, and this intermediate image is then passed through relay lens 30 and collection aperture 40 to the surface of the sensor array, such as the surface of array camera 20.

The illuminating path illuminates an area of the reticle 100. In order to image larger areas of the reticle or even illuminate the whole reticle a relative movement is provided between reticle 100 and between the illumination and collection path of the system. The reticle 100 can be moved, for example by a stage such as stage 70 that also supports the reticle 100.

System 10 acquires aerial images of reticle 100 that simulate the images that would be produced by the reticle 100 on the photoresist, when the reticle 100 is placed on an optical exposure system during a photolithographic process.

According to an embodiment of the invention the inspection system 10 can inspect reticles that are designed to be exposed in a wavelength that differs from the wavelength of light source 130.

Inspection system 10 has a processor 210 that is capable of executing aerial simulation software such as SOLID-C software SIGMA-C, from the United States. Processor 210 can include, or be connected to an image processor, that processes the signals provided from camera 20. It is noted that various processing tasks can be implemented by dedicated hardware, by software modules, by middleware or by a combination of the above. It is further noted that processor 210 can include multiple processors that can be positioned in various locations, integrated together and the like.

It is assumed that the reticle 100 is designed to be exposed by a 248 nm light and that light source 130 generates light of a second wavelength, such as 193 nm. In order to configure inspection system 10 to emulate the 248 nm photolithographic process, processor 210 defines the optical characteristics of system 10, including, for example $NA_i$ and $NA_c$.

The definition process usually includes the following stages: (i) receiving the optical characteristics of the photolithographic process (including the first wavelength 248 nm), (ii) providing the optical characteristics of the 248 nm lithographic process to the aerial simulation software and in response generating, by the aerial simulation software, a first aerial image of a certain portion of the reticle; (iii) determining, usually by an iterative process, the required $NA_i$ and the $NA_c$ of inspection system 10 such that when the inspection system 10 performs an inspection sequence, using a light of a second wavelength, such as 193 nm, it generates a second image that substantially equals the first image. This stage can include multiple iterations of the aerial simulation software.

Typically, the aerial simulation software provides various characteristics of the first image, including, for example, the critical dimensions of a structure that is included in the image, the image contrast level, the image NILS, and the like. The aerial simulation software can be executed until a second image of substantially same characteristics is provided. According to another aspect of the invention the first image and the images produced by the aerial simulation software can be compared by using image processing techniques, or even by a combination of image processing technique and characteristics based comparison.

Once the $NA_i$ and $NA_c$ are determined the collection aperture and illumination aperture are altered accordingly, so that the inspection system 10 can provide aerial images that simulate the 248 nm photolithographic process.

The inventors used $NA_c$ that ranges between 0.12 to 0.23 at steps of 0.005 while σ ranged between 0.3 to 0.9 at steps of 0.02. It is noted that these ranges and steps are provided as an example alone and do not intend to narrow the scope of the invention to these specific ranges and steps.

Those skilled in the art will appreciate that the aerial simulation software is fed with the possible $NA_i$ and $NA_c$ of system 10 prior performing the aerial image simulations.

Once the required $NA_i$ and $NA_c$ are determined the adjustment of system 10 can be done manually or automatically.

It is noted that once system 10 is set it can apply various comparison methods including, for example, die to die, cell to cell, die to database and the like. Some of these comparison methods were mentioned in U.S. Pat. No. 6,268,093, which is incorporated herein by reference.

Figure 2:
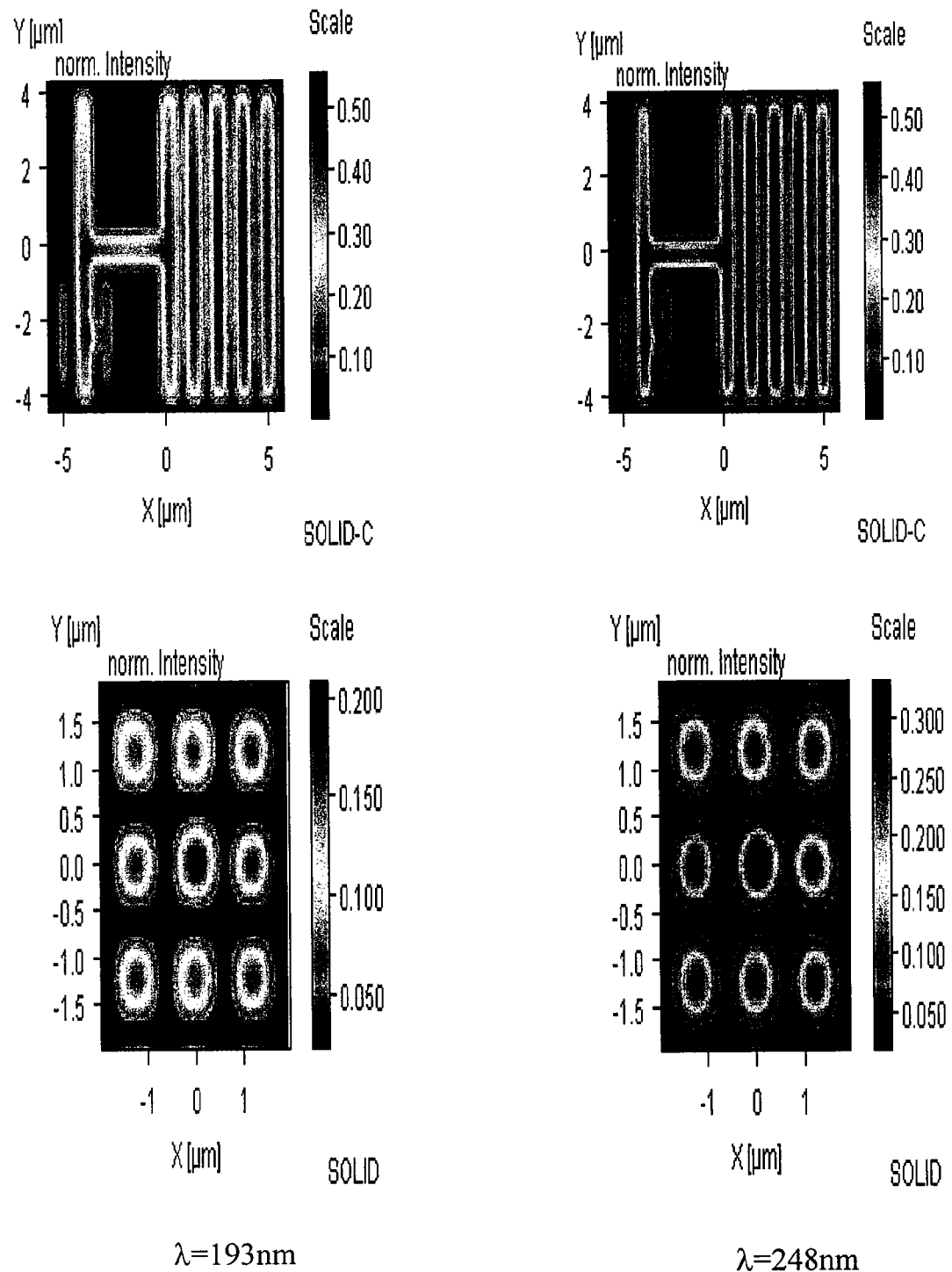
FIG. 2 shows simulated aerial images obtained under different optical characteristics, according to an embodiment of the invention.

FIG. 2 shows simulated aerial images obtained under different optical characteristics, according to an embodiment of the invention. The images at the right side of the drawing were simulated assuming that light of 248 nm is used, while the drawings on the left were simulated assuming that a 193 nm light was used.

FIG. 3 is a flow chart of method 300 for inspecting a reticle, according to an embodiment of the invention.

Method 300 starts by stage 310 of providing a reticle designed to be exposed by light of a first wavelength during a photolithography process. For example, reticle 100 that is designed such as to imprint certain patterns during a 248 nm lithographic process is placed on stage 70.

Stage 310 is followed by stage 320 of defining optical characteristics of an inspection system, whereas the optical characteristics include a second wavelength that differs from the first wavelength. For a non-limiting example, the first wavelength is 248 nm while the second wavelength is 193 nm. Yet for another example, processor 210 can receive the optical characteristics (including a first wavelength) of a photolithographic process and in response execute an aerial simulation software to define the optical characteristics of inspection system 10, given the first wavelength of light source 130.

Stage 320 conveniently involves defining a collection numerical aperture of the inspection system in response to the second wavelength and in response to at least one optical characteristic of the photolithographic process. Conveniently, stage 320 includes utilizing aerial simulation software.

Stage 320 may include defining an illumination numerical aperture of the inspection system in response to the second wavelength and in response to at least one optical characteristic of the photolithographic process.

Stage 320 is followed by stage 330 of configuring an inspection system in response to the defined optical characteristics. Stage 330 conveniently includes setting a collection numerical aperture of the inspection system in response to the defined collection numerical aperture.

According to an embodiment of the invention stage 330 includes setting a magnification optic, positioned at a collection path of the inspection system.

According to another embodiment of the invention stage 330 includes setting an aperture, such as but not limited to collection aperture 40, positioned at a collection path of the inspection system. Conveniently, stage 330 including setting an illumination numerical aperture of the inspection system in response to the defined illumination numerical aperture.

According to an embodiment of the invention, stage 330 includes setting a magnification optic, such as zoom lens 120, positioned at an illumination path of the inspection system. Conveniently, stage 330 includes setting an aperture, such as illumination aperture 110, positioned at an illumination path of the inspection system.

Stage 330 is conveniently followed by stage 340 of illuminating at least a portion of the reticle with light of the second wavelength to provide at least one image. This stage may include introducing a movement between the reticle 100 and the optical paths such as to illuminate larger areas of reticle 100 and even the whole reticle 100. Typically, stage 340 is followed by applying one or more comparison methods to determine the presence of reticle defects.

Stage 340 may include at least one of the following: (i) setting an illumination numerical aperture of the inspection system in response to the defined illumination numerical aperture; (ii) setting a magnification optic positioned at an illumination path of the inspection system; and/or (iii) setting an aperture positioned at an illumination path of the inspection system.

While the invention has been described herein using preferred embodiments thereof, it will be readily appreciated by those skilled in the art that various modifications in form and detail may be made therein without departing from the scope and spirit of the invention.

What is claimed is:

1. A method of inspecting a reticle, comprising:
   using aerial simulation software, generating a first aerial image of a reticle for optical characteristics of a photolithogaphic process which uses said reticle, said optical characteristics including use of light of a first wavelength;
   using the aerial simulation software, iteratively generating second aerial images of the reticle for optical characteristics of a reticle inspection station which uses light of a second wavelength and comparing each second aerial image to the first aerial image until selecting one of the second aerial images that is substantially equal to the first aerial image;
   defining optical characteristics of the reticle inspection system so as to produce aerial images of the reticle as defined by the selected one of the second aerial images,
   configuring the inspection system according to the defined optical characteristics so that the inspection system emulates the photolithographic process while utilizing light of the second wavelength; and
   inspecting the reticle by illuminating at least a portion of the reticle using light of the second wavelength within the inspection system configured according to the defined optical characteristics to produce an image and using a comparison technique to identify defects in the reticle from said image.

2. The method of claim 1 wherein defining optical characteristics comprises defining a collection numerical aperture of the inspection system.

3. The method of claim 2 wherein configuring comprises setting a collection numerical aperture of the inspection system in response to the defined collection numerical aperture.

4. The method of claim 2 wherein configuring comprises setting a magnification optic positioned in a collection path of the inspection system.

5. The method of claim 2 wherein configuring comprises setting an aperture positioned in a collection path of the inspection system.

6. The method of claim 1 wherein defining optical characteristics comprises defining an illumination numerical aperture of the inspection system.

7. The method of claim 6 wherein configuring comprises setting an illumination numerical aperture of the inspection system in response to the defined illumination numerical aperture.

8. The method of claim 6 wherein configuring step comprises setting a magnification optic positioned in an illumination path of the inspection system.

9. The method of claim 6 wherein configuring comprises setting an aperture positioned in an illumination path of the inspection system.

10. The method of claim 6 wherein defining optical characteristics comprises defining a collection numerical aperture of the inspection system.

* * * * *